United States Patent [19]

Rhodes

[11] Patent Number: 5,346,687
[45] Date of Patent: * Sep. 13, 1994

[54] DIRECT RADIOLABELING OF ANTIBODY AGAINST STAGE SPECIFIC EMBRYONIC ANTIGEN FOR DIAGNOSTIC IMAGING

[75] Inventor: Buck A. Rhodes, Albuquerque, N. Mex.

[73] Assignee: Rhomed Incorporated, Albuquerque, N. Mex.

[*] Notice: The portion of the term of this patent subsequent to Jan. 7, 2009 has been disclaimed.

[21] Appl. No.: 816,476

[22] Filed: Jan. 3, 1992

Related U.S. Application Data

[63] Continuation-in-part of Ser. No. 391,474, Aug. 9, 1989, Pat. No. 5,078,985.

[51] Int. Cl.$^5$ .............. A61K 49/02; A61K 43/00; A61K 39/395; C07B 59/00
[52] U.S. Cl. .............. 424/1.49; 530/391.5; 530/391.3; 530/866
[58] Field of Search .............. 424/1.1, 1.49, 1.53; 530/391.3, 391.5, 402, 866

[56] References Cited

U.S. PATENT DOCUMENTS

| | | | |
|---|---|---|---|
| 3,812,264 | 5/1974 | Nouel | 424/1.1 |
| 4,421,735 | 12/1983 | Haber et al. | 424/1.1 |
| 4,424,200 | 1/1984 | Crockford et al. | 424/1.1 |
| 4,472,371 | 9/1984 | Burchiel et al. | 424/1.1 |
| 4,478,815 | 10/1984 | Burchiel et al. | 424/1.1 |
| 4,479,930 | 10/1984 | Hnatowich | 424/1.1 |
| 4,622,420 | 11/1986 | Meares et al. | 562/443 |
| 4,668,503 | 5/1987 | Hnatowich | 424/1.1 |
| 4,670,545 | 6/1987 | Fritzberg et al. | 534/14 |
| 4,877,868 | 10/1989 | Reno et al. | 530/390 |
| 4,917,878 | 4/1990 | Thakur | 424/1.1 |
| 5,011,676 | 4/1991 | Thakur | 424/1.1 |
| 5,053,493 | 10/1991 | Pak et al. | 530/402 |
| 5,061,641 | 10/1991 | Shochat et al. | 436/545 |
| 5,078,985 | 1/1992 | Rhodes | 424/1.1 |
| 5,102,990 | 4/1992 | Rhodes | 424/1.1 X |
| 5,116,596 | 5/1992 | Bremer et al. | 424/1.1 |
| 5,128,119 | 7/1992 | Griffiths | 424/1.1 |

FOREIGN PATENT DOCUMENTS

| | | | |
|---|---|---|---|
| 271806 | 6/1988 | European Pat. Off. | |
| 419203 | 3/1991 | European Pat. Off. | A61K 49/02 |
| 2043459 | 5/1969 | France | A61K 27/00 |
| 04164 | 7/1987 | PCT Int'l Appl. | A61K 49/02 |
| 07382 | 10/1988 | PCT Int'l Appl. | A61K 49/02 |
| 15626 | 12/1990 | PCT Int'l Appl. | A61K 49/02 |
| 02547 | 3/1991 | PCT Int'l Appl. | A61K 49/02 |

OTHER PUBLICATIONS

"The Labeling of High Affinity Sites of Antibodies with 99MTc," by Chang H. Paik et al., Int. J. Nucl. Med. Biol., vol. 12, No. 1, pp. 3–8 (1985).

Thakur, M. L., et al., "Tc-99m Labeled Monoclonal Antibody (Mab) in Patients with Inflammatory Diseases," 1991 Abstract Form, No. 31857, Soc. Nucl. Med. 38th Ann. Mtg., Cincinnati Convention Ctr., Cincinnati, Ohio, Jun. 11–14, 1991.

Thakur, M. L., et al., "Monoclonal Antibodies as Agents for Selective Radiolabeling of Human Neutrophils," J. Nucl. Med., vol. 29, No. 11, pp. 1817–1825, (1988).

(List continued on next page.)

Primary Examiner—Robert L. Stoll
Assistant Examiner—John M. Covert
Attorney, Agent, or Firm—Deborah A. Peacock; Donovan F. Duggan

[57] ABSTRACT

Antibody against stage specific embryonic antigen-1 is radiolabeled by direct means with a radionuclide for use in detection of occult abscess and inflammation. Radiolabeling is accomplished by partial reduction of the disulfide bonds of the antibody using Sn(II), or using other reducing agents followed by the addition of Sn(II), removal of excess reducing agent and reduction by-products, and addition of a specified amount of radionuclide reducing agent, such as stannous tartrate. The resulting product may be store frozen or lyophilized, with radiolabeling accomplished by the addition of the radionuclide.

20 Claims, No Drawings

OTHER PUBLICATIONS

Pak, K. Y., et al., "A Rapid and Efficient Method for Labeling IgG Antibodies with Tc-99m and Comparison to Tc-99m FAB' Antibody Fragments," Scientific Papers, Proceedings of the 36th Annual Meeting, J. Nucl. Med., vol. 30, No. 5, p. 793 (No. 268), (1989).

Granowska, M., et al., "A Tc-99m Labelled Monoclonal Antibody, PR1A3, for Radioimmunoscintigraphy, RIS, of Colorectal Cancer," Proceedings of the 36th Annual Meeting, J. Nucl. Med., vol. 30, p. 748 (No. 80), (1989).

Ballou, B. et al., "Tumor Radioimmunolocation: Differential Antibody Retention of Antigenic Normal Tissue and Tumor," J. Immunol., vol. 132, No. 4, pp. 2111-2116, (Apr. 1984).

Skubitz, K., et al., "Monoclonal Antibodies that Recognize Lacto-N-Fucopentaose III (CD15) React with the Adhesion-Promoting Glycoprotein Family (LFA-1/HMAC-1/GP 150,95) and Cr1 on Human Neutrophils[1,2], " J. Immun., vol. 139, No. 5, pp. 1631-1639, (Sep. 1987).

Wensel, Theodore G., et al., "Bifunctional Chelating Agents for Binding Metal Ions to Proteins," S. W. Burchiel and B. A. Rhodes, Eds., *Radioimmunoimaging and Radioimmunotheraphy*, pp. 185-196, (1983).

Krejcarek, Gary E., et al., "Covalent Attachment of Chelating Groups to Macromolecules," Biochem. & Biophy. Res. Comm., vol. 77, No. 2, pp. 581-585, (1977).

Baidoo, Kwamena E., et al., "$^{99m}$Tc Labeling of Proteins: Initial Evaluation of a Novel Diaminedithiol Bifunctional Chelating Agent," Cancer Res. (Supp). vol. 50, pp. 799s-803s, (Feb. 1990).

Som. P., et al., "Radioimmunoimaging of Experimental Thrombi in Dogs Using Technetium-99-m-Labeled Monoclonal Antibody Fragments Reactive with Human Platelets," J. Nucl. Med., vol. 27, No. 8, pp. 1315-1320, (Aug. 1986).

Rhodes, Buck A., et al., "Technetium-99m Labeling of Murine Monoclonal Antibody Fragments," J. Nucl. Med., vol. 27, No. 6, pp. 685-693, (May 1986).

Schwarz, A., et al., "A Novel Approach to Tc-99-m-Labeled Monoclonal Antibodies," Poster Sessions, Proceedings of 34th Ann. Mtg., J. Nucl. Med., vol. 28, No. 4, p. 721 (No. 695), (Apr. 1987).

Knowles, B. B., et al., "Murine Embryonic Antigen (SSEA-1) is Expressed on Human Cells and Structurally Related Human Blood Group Antigen I is Expressed on Mouse Embryos," Dev. Biol., vol. 93, pp. 54-58, (1982).

Solter, D. et al., "Monoclonal Antibody Defining a Stage-Specific Mouse Embryonic Antigen (SSAE-1)," Proc. Natl. Acad. Sci., vol. 75, No. 11, pp. 5565-5569, (Nov. 1978).

Fox, Niles, et al., "Immunohistochemical Localization of the Mouse Stage-Specific Embryonic Antigen 1 in Human tissues and Tumors," Cancer Res., vol. 43, pp. 669-678, (Feb. 1983).

Gooi, H. D. et al., "Stage-Specific Embryonic Antigen Involves α 1→3 Fucosylated Type 2 Blood Group Chains," Nature (London), vol. 292, No. 5819, pp. 156-158, (Jul. 1981).

Andrews, Robert G., et al., "Nonlymphoblastic leukemia-Associated Antigens Identified by Monoclonal Antibodies," S. Sell et al., Eds., Human Press, Clifton, N.J. Ch. 8, pp. 167-203, (1985).

Rhodes et al., *J. Nucl. Med.*, vol. 27, (1986) "Techetium-99m Labeling . . . " pp. 685-693.

DIRECT RADIOLABELING OF ANTIBODY AGAINST STAGE SPECIFIC EMBRYONIC ANTIGEN FOR DIAGNOSTIC IMAGING

LICENSE RIGHTS

The U.S. Government has a paid-up license in this invention and the right in limited circumstances to require the patent owner to license others on reasonable terms as provided for by the terms of Grant No. DE-FG04-89ER60899 awarded by the Department of Energy.

CROSS-REFERENCE TO RELATED APPLICATIONS

This application is a continuation-in-part application of U.S. Pat. No. 5,078,985, issued Jan. 7, 1992, entitled *Radiolabeling Antibodies and Other Proteins with Technetium or Phendium by Regulated reduction,* and is related to U.S. Pat. No. 5,102,990 issued apr. 7, 1992, entitled *direct Radiolabeling of Antibodies and Other Proteins with Technetium or Phenium,* a divisional application, U.S. application Ser. No. 07/815,122, filed Dec. 27, 1991, now abandoned entitled *Method for Radiolabeling Antibodies and Other Proteins by Regulated Reduction,* the teachings of all of which are incorporated herein by reference. A related U.S. application Ser. No. 07/816,477, entitled *Direct Labeling of Antibodies and Other Proteins with Metal Ions* is being filed concurrently herewith, and the specification thereof is incorporated herein by reference.

BACKGROUND OF THE INVENTION

1. Field of the Invention (Technical Field)

This invention relates to a method and composition for radiolabeling monoclonal antibodies against stage specific embryonic antigen-1 with the radioisotope technetium-99m, and further providing for use of the radiolabeled monoclonal antibody preparation for detection of infections and inflammation.

2. Background Art

The use of radioisotopes to label proteins is well known. These compositions can be used in in vitro assays; can be administered to the human body to visualize or monitor functioning of various parts of the body or to determine the presence and location of particular antigens, antibodies, hormones or the like; and can be used in the treatment of various disease states.

Technetium-99m has been utilized to radiolabel proteins, chelating agents, phosphonate bone scanning compositions and the like by a technique which utilizes sodium pertechnetate wherein the technetium initially is in the +7 state. Technetium-99m is generally available only as sodium pertechnetate. The pertechnetate comes into contact with a reducing agent, such as stannous chloride, for the technetium to be reduced to the +3, +4 or +5 oxidation state. The technetium must be maintained in this reduced state in order to maintain the chemical bond between the technetium molecule and the protein, chelating agent or like substrate being radiolabeled. It is also necessary that the technetiumbe firmly bound to the protein such that the reduced technetium is not transferred to other molecules or other proteins present in the assay, patient's blood or other media in which the radiolabeled substance will be utilized.

Several different methods have been utilized to radiolabel proteins, particularly monoclonal antibodies, with technetium-99m. The methods involve two general approaches. One approach is indirect in which a bifunctional chelating agent is attached to the protein via one functional group and the technetium-99m is attached via the other functional, or chelating, group. This method was introduced by Krejcarek, G. E. and Tucker, K. L. ("*Covalent Attachment of Chelating Groups to Macromolecules,*" *Biochemical and Biophysical Research Communications* 77:581–585, 1977) and has been widely employed in many variations using a wide variety of bifunctional chelating agents such as described in the review of Wensel and Meares (Wensel, T. G. and Meares, C. F., "'Bifunctional' Chelating Agents for Binding Metal Ions to Proteins," *Radioimmunoimaging and Radioimmunotherapy,* S. W. Burchiel and B. A. Rhodes, eds., Elsevier Publishing Co., New York, 1983, pp 185–196). Other methods are disclosed by Hnatowich, D. J., U.S. Pat. Nos. 4,668,503 and 4,479,930; by Meares, C. F. et. al., U.S. Pat. No. 4,622,420; by Haber, E., and Khaw, B. A., U.S. Pat. No. 4,421,735; and by Fritzberg, A. R., and Kastna, S., U.S. Pat. No. 4,670,545, and by Baidoo, K. E., et. al., "$^{99m}$Tc Labeling of Proteins: Initial Evaluation of Novel Dtamtnedithiol Bifunctional Chelating Agent," Cancer Res (Supp) 50:799s–803s, 1990. The bifunctional chelate methods all present significant limitations, including the complexity of the radiolabeling procedure, the time required to accomplish radiolabeling, and the presence of substances which may affect the protein.

The other general approach is direct labeling. Although several direct methods have been reported, the first direct method capable of providing a sufficiently strong bond between the protein and the technetium-99m for in vivo applications was the direct or pretinning method described in U.S. Pat. No. 4,424,200, entitled *Method for Radiolabeling Proteins with Technetium-99m,* to Crockford, D. R., and Rhodes, B. A. In this method, a single reduction compound, consisting of stannous [Sn(II)] chloride and other salts which serves both to reduce the protein, thereby exposing the disulfide bonds, and to reduce the sodium pertechnetate, is used. With this method, many proteins can be successfully radiolabeled with $^{99m}$Tc. Several investigators have reported on the use of this method (Rhodes, B. A., et. al., "Technetium-99m labeling of murine monoclonal antibody fragments," *J Nucl Med* 27:685–693, 1986; Som, P., et. al., "*Radioimmunoimaging of experimental thrombi in dogs using technetium*-99m-labeled monoclonal antibody fragments reactive with human platelets," *J Nucl Med* 27:1315–1320, 1987).

Equivalent methods for direct labeling have been reported (Schwarz, A., and Steinstruaber, A., "A novel approach to Tc-99m-labeled monoclonal antibodies," *J Nucl Med* 28:721, 1987; Pak, K. Y., et. al., "A rapid and efficient method for labeling IgG antibodies with Tc-99m and comparison to Tc-99m Fab'". *J Nucl Med* 30:793, 1989; Granowska, M., et. al., "A Tc-99m-labeled monoclonal antibody, PR1A3, for radioimmunoscintigraphy," *J Nucl Med* 30:748, 1989). In the equivalent methods disulfide reducing agents other than stannous salts were used. Pak et. al. used dithiothreitol to reduce the disulfide bonds of the antibody; Swartz and Steinsbruaber, and Granowska et. al. used 2-mercaptoethanol. Also some of these investigators (Swartz and Stetnsbruaber, and Granowska et. al.) reduced the Tc-99m prior to adding it to the reduced antibody, which adds steps to the original procedure.

Reno, J. W., et. al., U.S. Pat. No. 4,877,868, *Radionuclide Antibody Coupling*, uses dithiothreitol (DTT) to reduce the disulfide groups of the protein, then protect the reactive sulfides with Zn (II) or other sulfhydryl group dertvatiztng reagents. Tartrate salts are used to complex and transfer the reduced radionuclide. This method uses potentially toxic chemicals, such as dithiothreitol, to reduce the antibody. It also requires multiple steps to radiolabel the protein.

Thakur, M. L., U.S. Pat. No. 5,011,676, *Method to Directly Radiolabel Antibodies for Diagnostic Imaging and Therapy*, used sodium ascorbate to reduce the disulfide groups of antibodies. This method was used with anti-SSEA-1 IgMneutrophil specific antibody. However, this method cannot be adapted to single-step, direct labeling; it is required to reduce the radionuclide prior to adding the radionuclide to the sodium ascorbate reduced protein. In a preferred embodiment of the Thakur method, a separate vial is utilized, in which sodium dithionite is used to reduce the radionuclide, producing dithionite reduced radionuclide, and the reduced radionuclide is then added to the sodium ascorbate reduced protein.

In U.S. Pat. No. 4,917,878, *Novel Use of a Radiolabelled Antibody Against Stage Specific Embryonic Antigen for the Detection of Occult Abscesses in Mammals* to M. L. Thakur, a class of antibody, useful when radiolabeled for the diagnosis of hidden infections and inflammations in man, is identified. This class of antibody comprises antibody against stage specific embryonic antigen-1 (hereinafter "SSEA-1" or "anti-SSEA-1"). The SSEA-1 antigen is known to be expressed on human granulocytes. Anti-SSEA-1 antibodies have high specificity for human neutrophils, and thus preferentially bind to human neutrophils in vivo.

SUMMARY OF THE INVENTION (DISCLOSURE OF THE INVENTION)

In accordance with the present invention, a method is provided for radiolabeling monoclonal antibodies, or fragments thereof, against stage specific embryonic antigen-1 with a radionuclide, in which a reducing agent is used to reduce the disulfide bonds in the protein; excess reducing agent, reaction by-products and any impurities are removed; and an optimum concentration of radionuclide reducing agent is added.

In the preferred method, the antibody against stage specific embryonic antigen-1 is stably radiolabeled with a radionuclide by incubating the antibody against stage specific embryonic antigen-1 with a first reducing agent, the period of incubation being sufficient to reduce available disulfide bonds to thiolate groups while preventing excessive fragmentation of the antibody; then purifying the reduced antibody to substantially remove the first reducing agent and impurities; adding a source of Sn (II) agent to the reduced antibody in a sufficient amount to form Sn (II)-containing and sulfur-containing complexes and to reduce the radionuclide; and radiolabeling the purified reduced antibody by adding the radionuclide, whereby the Sn (II) agent reduces the radionuclide and the reduced radionuclide and reduced antibody form radionuclide-containing and sulfur-containing complexes.

The order of the steps may be altered, and the method will still produce radiolabeled antibody proteins; the claims are therefore not limited to the order of steps presented. Specifically, it is possible, and in some cases advantageous, to add the Sn (II) to form Sn (II)-containing and sulfur-containing complexes prior to removing excess reducing agent from the antibody substrate. In this way, oxidation of thiolate groups or reformation of disulfide bonds and other cross-linkages is immediately prevented.

In an alternate method, the antibody against stage specific embryonic antigen-1 is stably radiolabeled with a radionuclide by incubating the antibody against stage specific embryonic antigen-1 with a Sn (II) agent, the period of incubation being sufficient to reduce available disulfide bonds to thiolate groups and allow formation of Sn (II)-containing and sulfur-containing complexes, while preventing excessive fragmentation of the antibody; then purifying the reduced antibody to remove uncomplexed Sn (II) agents and other impurities yet retaining Sn (II) in a sufficient amount to reduce the radionuclide and not generate significant radio-chemical impurities; and radiolabeling the purified antibody with the Sn (II)-containing and sulfur-containing complexes by adding the radionuclide, whereby the Sn (II) agent reduces the radionuclide and the reduced radionuclide forms radionuclide-containing and sulfur-containing complexes.

In the preferred method, the first reducing agent can include such substances as 2-mercaptoethanol; 1,4 dithiothreitol; 2,3 dihydroxybutane-1; 4 dithiol; 2-aminoethanethiol HCl; 2-mercaptoethylamine; thioglycolate; cyanide; cysteine; reduced glutathione; Sn (II); Cu (I); and Ti (II). It is possible to attach the first reducing agent to a solid phase.

In either method, the source of Sn (II) agent can be present in a solution comprising alkali metal tartrate having a pH of between approximately 5.0 and 6.0. Similarly, in either method the source of Sn (II) agent can include such substances as stannous tartrate, stannous glucoheptonate, stannous gluconate, stannous phosphonate, stannous chloride, and stannous fluoride.

In both methods, the antibody against stage specific embryonic antigen-1 can be a product of the MCA-480 hybridoma. The antibody can also be a product of the B37.2.1 hybridoma.

After addition of the Sn (II) agent, the Sn (II)-containing and sulfur-containing complexes can be frozen in a vial, and maintained for an indefinite period before labeling by the addition of the medically useful metal ion to the vial. Similarly, after addition of the Sn (II) agent, the product can be lyophilized in a vial, and maintained for an indefinite period before labeling.

In both methods, the preferred radionuclide is technetium-99m in the form of sodium pertechnetate. However, other radionuclides can be used, including radioisotopes of indium, gold, silver, mercury, technetium, rhenium and copper.

Products can be made by either method, and the product used for the detection of occult abscess and inflammation. It is also possible to make a product using either method in which 85 percent or more of the radionuclide is strongly bonded to the antibody. The product can be used in diagnostic imaging modalities such as gamma scintigraphy, magnetic resonance imaging, and positron emission tomography. Using either method, it is possible to develop a product which does not require a purification step of the radio-pharmaceutical after radiolabeling but prior to in vivo administration.

Accordingly, it is an object of the present invention to provide a method for direct labeling of anti-SSEA-1 antibody with technetium-99m, which method will eliminate undesirable fragments or otherwise degraded protein components from the final product.

It is a further object of the present invention to provide a method which will result in increased radiolabeling efficiencies utilizing technetium-99m as the radioisotope.

It is a further object of the present invention to provide a method to label antibody against stage specific embryonic antigen with radionuclides without loss of the biological function of the antibody due to the labeling process.

Another object of the present invention is to provide a method and product which will permit radiolabeling to be accomplished by the end user using a single vial, containing both reduced antibody and stannous ions, and further containing a means to maintain low quantities of stannous ions while protecting against oxidation loss, which method requires only a single step to accomplish radiolabeling, being the introduction of radionuclide, preferably technetium in the form of sodium pertechnetate.

Other objects, advantages, and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENTS (BEST MODES FOR CARRYING OUT THE INVENTION)

The present invention provides a method for radiolabeling monoclonal antibodies, or fragments thereof, against stage specific embryonic antigen-1 with a radionuclide, in which a reducing agent is used to reduce the disulfide bonds in the protein; excess reducing agent, reaction by-products and any impurities are removed; and an optimum concentration of radionuclide reducing agent is added.

Any antibody against stage specific embryonic antigen-1 which contains one or more disulfide bonds or one or more monosulfides can be radiolabeled in accordance with this invention. Representative suitable substrates include antibodies, or antibody fragments, of any species, and including both polyclonal and monoclonal antibodies made by any means, as well as chimeric and genetically engineered antibodies, and antibody fragments of all of the foregoing. This includes immunoglobulins of any class, such as IgG, IgM, IgA, IgD or IgE; of any species origin, including murine, human beings, chimeric antibodies or hybrid antibodies with dual or multiple antigen or epitope specificities; fragments of all of the foregoing, including F(ab')2, F(ab)2, Fab', Fab and other fragments, including hybrid fragments; and further includes any immunoglobulin or any natural, synthetic or genetically engineered protein that functionally acts like an antibody by binding to a specific antigen to form a complex. The term "antibody" or "antibodies", and the phrase "monoclonal antibody component", as used throughout the specification and claims is intended to include all such antibodies and antibody fragments.

In Rhodes, B. A., U.S. Pat. No. 5,078,985, issued Jan. 7, 1992, entitled *Radiolabeling Antibodies and Other Proteins with Technetium or Ohenium by regulated Reduction*, a method is taught in which proteins are radiolabeled with radionuclides, such as of technetium or rhenium, by a process in which the disulfide bonds of the protein are first partially reduced with stannous salts or other disulftde reducing agents, all substances other than the desired reduced protein removed, by size exclusion chromatography or other purification means, and a specified, smaller amount of the radionuclide reducing agent, such as a stannous salt, is added to the reduced protein in a manner such that further reduction of the protein is limited.

In Rhodes, B. A., U.S. Pat. No. 5,102,990, issued Apr. 7, 1992, entitled *direct Radiolabeling of antibodies and Other Proteins with Technetium or Ohenium*, a method, product and kit is provided, wherein proteins containing one or more disulfide bonds are radiolabeled with radionuclides for use in diagnosis and treatment of a variety of pathologic conditions. Radiolabeling is accomplished by partial reduction of the disulfide bonds of the protein using Sn (II), or using other reducing agents followed by the addition of Sn (II), removal of excess reducing agent and reduction by-products, and addition of a specified amount of radionuclide reducing agent, such as stannous tartrate, with the addition accomplished in such a manner that further reduction of the protein is limited.

The methods and kits of both the '474 and '275 applications are useful in the present invention. The discussions therein pertaining to technetium and rhenium are also appropriate for the other radiometals and metal ionic forms described herein. Accordingly, the teachings of both of these applications are incorporated herein by reference.

In Rhodes, B. A. and Zamora, P. O., a U.S. Pat. application entitled *direct Labeling of antibodies and Other Proteins with Metal Ions* filed concurrently herewith, a method is taught in which a protein substrate containing monosulfides or disulfide bonds is labeled with a medically useful metal ion by the following method:

a) incubating the protein with a reducing agent to reduce some or all of the disulfide bonds to thiolate groups, or to maintain monosulfides as thiolate groups;

b) removing excess reducing agent from the protein substrate containing thiolate groups;

c) adding a source of Sn (II) agent to the thiolate-containing protein preparation in an amount sufficient to form Sn (II)-containing and sulfur-containing complexes; and, d) adding a medically useful metal ion whereby the metal ion displaces the Sn (II) in the Sn (II)-containing and sulfur-containing complexes and the metal ion and thiolate-containing protein form metal ion-containing and sulfur-containing complexes.

The medically useful metal ions includes ionic forms of the elements iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium and astatine. Some medically useful metal ions are radioactive, such as radionucltdic isotopes of indium, gold, silver, mercury, technetium, rhenium and copper. The medically useful metal ion can also be paramagnetic. The product resulting from the application of this method can be used for gamma scintigraphy, specific photon emission computerized tomography, magnetic resonance imaging, positron emission tomography and radiotherapy. The discussions therein pertaining to medically useful metal ions are also appropriate for use with the antibody against stage specific embryonic antigen described herein. Accordingly, the teachings of this application are incorporated herein by reference.

There is a wide variety of clinical conditions characterized by severe inflammation. Hidden, or occult abscesses, are particularly difficult to diagnose accurately. These lesions can be caused by a variety of bacteria and may be localized in any organ system. The location can be crucial to the choice of antibiotic or other therapy. Other significant conditions involving inflammatory foci include inflammatory bowel disease, appendicitis, opportunistic infections in patients with AIDS, and the inflammation associated with organ transplants and surgically implanted prostheses. Acute inflammatory disease may be life threatening; some types of abscesses have an overall mortality of 40%. Prompt diagnosis and treatment is crucial to patient survival.

Anti-SSEA-1 is used to refer to a specific murine IgM antibody originally developed by researchers at the Wistar Institute, Philadelphia, PA. (Solter, D., Knowles, B. B., "Monoclonal antibody defining a stage-specific mouse embryonic antigen (SSEA-1),"]*Proc Natl Acad Sci USA* 75:5565–5569, 1978.) This antibody is also referred to by its parent hybridoma cell line Wtstar number, MCA-480. The antibody, originally developed by Solter and Knowles, recognizes a stage-specific mouse embryonic antigen. The antigen was found to involve the alpha 1-3 fucosylated type 2 blood group chains and is expressed by a number of human tissues. (Gooi, H. C., Feizi, T., Kapadia, A., et. al., "Stage-specific embryonic antigen (SSEA-1) involves the 3-fucosylated type 2 precursor chain," *Nature (London)* 292:156–158, 1981; Knowles, B. B., Rappoport, 3., Solter, D., "Murine embryonic antigen (SSEA-1) is expressed on human cells and structurally related human blood group antigen I is expressed on murine embryos," *Der Biol* 93:54–58, 1982.) This antigen is expressed primarily on human granulocytes, is a highly immunogenic epitope, and has been used to generate a large number of monoclonal antibodies; see review of Andrews and Bernstein. (Andrews R. G., Bernstein, I. D., "Nonlymphoblastic leukemia-associated antigens identified by monoclonal antibodies," Monoclonal Antibodies in Cancer, S Sell, R Reisfeld, eds., Humana Press, Clifton, NJ, pp. 167–203, 1985.) The Wistar anti-SSEA-1 produced by MCA-480 was originally evaluated by M. L. Thakur for use in the ex vivo labeling of human granulocytes and was found to be superior to nine other antibodies also evaluated for this purpose. (Thakur, M. L., Richard, M. D., White III, F. W., "Monoclonal antibodies as agents for selective radiolabeling of human neutrophils," *J Nucl Med* 29:1817–1825, 1988.) It has recently been used to target inflammations and infections in human clinical trials. Thakur, M. L., Marcus, C. S., Henneman, P. et. al., "$^{99m}$Tc-labeled monoclonal antibody (MAB) in patients with inflammatory diseases," Presented at the 38th Ann. Mtg. Soc. Nucl. Med., Cincinnati, OH, Jun. 11–14, 1991.

In initial clinical trials, anti-SSEA-1 murine monoclonal antibody made by the MCA-480 cell line was conjugated with $^{99m}$Tc in one of two ways. Patients in Group A were imaged with antibody labeled by using a bifunctional chelate method, employing c-DTPA conjugate antibody labeled with $Na_2S_2O_4$-reduced $^{99m}$Tc; patients in Group B were imaged with the same antibody labeled by using the multiple step sodium ascorbate-based, direct labeling method of Thakur, U.S. Pat. No. 5,011,676, again with $Na_2S_2O_4$-reduced $^{99m}$Tc. There were 5 patients in Group A (3 male, 2 female) and 7 patients in Group B (6 male, 1 female), for a total of 12 patients.

All patients were admitted to the study to localize or rule out the presence of inflammation/infection. Imaging studies and follow up care took place at Harbor-UCLA Medical Center, Torrance, CA. In all cases, the site(s) of inflammation/infection were identifiable by gamma scintigraphy within three hours of administering the imaging reagent, and in most cases, were apparent much sooner. Sites of inflammatory foci were generally confirmed by radiologic, pathologic or surgical observation. The conditions imaged in Group A patients included early, moderate, and perforated appendicitis; early psoas abscess; and inflammation secondary to ascariasts. Group B included 3 immunosuppressed patients with unknown sites of infection (1 immunosuppressed alcoholic and 2 HIV+patients), whose inflammatory foci were subsequently identified as lymphadenopathy secondary to possible appendicitis and multiple superficial lesions; pericarditis and mediastinal lymph node infection; and acute tubular necrosis secondary to gentamycin toxicity, respectively. Other conditions imaged in patients from Group B include perinephric abscess, appendicitis, and osteomyelitis.

Distribution of radioactivity at approximately 2 hours after injection, for 9 of the patients (6 for bladder), was liver (49.0±3.20%), spleen (7.7±0.99%), red marrow (14.0±1.80%), lungs (4.5±0.79%), kidneys (2.4±0.40%), gall bladder (0.60±0.08), thyroid (0.19±0.03) and bladder (1.3±0.45%). Urine activity (percent of administered activity per hour) was 1.3±0.37%/hour. The percent of administered activity found in the blood (all cells +plasma) at approximately 2 hours was 31±8.0% (3 patients).

For all Group A patients, the activity bound to neutrophils ranged from 14.1% (neutrophil count of $3.2 \times 10^3$ cells/µl) to 44.2% (neutrophil count of $14.1 \times 10^3$/µl). The radioactivity associated with other blood elements was 9.1±1.3% on lymphocytes, 2.8±1.2% on platelets, and 1.6 ±% on red blood cells.

Biodistribution studies in the two HIV+patients from Group B showed the 1-hour postinjection distributions of radioactivity to be liver (42.8 and 44.3%), spleen (3.5 and 11.2%), bone marrow (2.1 and 0.9%), lungs (8.3 and 7.8%), kidneys (2.0 and 1.0%), bladder (0.5 and 0.2%), gall bladder (1.1 and 0.9%), thyroid (0.2 and 0.3%), and heart (5.0 and 3.6%). For all Group B patients, the radioactivity associated with neutrophils was 17.7±7.7%. (Neutrophil counts in Group B patients ranged from $1.3 \times 10^3$ cells/µl to $16.2 \times 10^3$ cells/µl.) The radioactivity associated with other blood elements was 11.3±2.1% on lymphocytes, 2.4±0.9% on platelets, 2.4±1.1% on red blood cells, and 67.3±9.0% in plasma.

In addition to the efficacy and biodistribution data described above, other information about efficacy and safety was obtained from the results of these initial studies. No side effects resulting from administration of the radiolabeled antibody were observed, even when the radio-pharmaceutical was administered as an I.V. bolus or given to a patient with the possible contraindication of a history of asthma. Using this reagent, SPECT scanning and flow studies were done on several patients, resulting in more definitive diagnoses than could be obtained through other modalities.

When Thakur evaluated the anti-SSEA-1 antibody, he found that human neutrophils have $5.1 \times 10^5$ antigenic determinants per cell. He observed that when an average of 10% of the available surface antigens were bound to anti-SSEA-1, the phagocytic ability and nylon wool adherence were approximately 70% and 80% that of respective control cells. At 4% or lower antigenic saturation, he observed no apparent changes in cell function.

A report by Skubitz and Snook shows that antibodies which react with lacto-N-fucopentaose III, such as anti-SSEA-1, react with five distinct neutrophil surface proteins. (Skubitz, K. M., Snook II, R. W., "Monoclonal antibodies that recognize 1-1acto-3-fucopentaose II (CD15) react with the adhesion-promoting glycoprotein family (LFA-1/HMAC-1/GP 150,95) and CR1 on human neutrophils," *J Immunol* 139:1631–1639, 1987.) The implication of this observation is that the effect of antibody binding to these surface molecules will depend on the relative binding to particular molecules and the role of the molecules in the behavior of the cells. Goot et. al. show that anti-SSEA-1 does not show equivalence in binding to the various oligosaccharide determinants of these surface molecules.

Non-specific binding of monoclonal antibodies has often limited the clinical utility of tagged antibodies tested for clinical applications. This property of anti-SSEA-1 made by MCA-480 has been studied previously. Fox et. al. tested 47 human tissues. (Fox, N., Damjanov, I., Knowles, B.B., et. al., "Immunohistochemical localization of the mouse stage specific embryonic antigen 1 in human tissues and tumors," *Cancer Res* 43:669–678, 1983.) In each tissue where SSEA-1 was detected, reactivity was always limited to the epithelial components. With the exception of the central nervous system, no reactivity was detected on the stromal or connective elements in any tissue. Ballou et. al., using immunoperoxidase microscopy, found that SSEA-1 was present on several normal mouse tissues, especially kidney and brain, yet there was no significant retention of in vivo injected, radiolabeled anti-SSEA-1 by any of these tissues. (Ballou, B., Jaffe, R., Taylor, R. J., et. al., "Tumor radioimmunolocation: differential antibody retention by antigenic normal tissue and tumor," *J. Immunol* 132:2111–2116, 1984.)

For imaging of infections or inflammation by labeling neutrophils with anti-SSEA-1, the high density of antigenic sites of the circulating neutrophils provides an immediately available primary binding site. Thus, the known, alternative binding sites do not interfere with tagging of the neutrophils or with the ability of the neutrophils to carry the radionuclide to the target lesions.

The method of U.S. Pat. No. 4,917,878 is limited to teaching the use of anti-SSEA-1 antibody radiolabeled by means of a bifunctional chelating agent which links the antibody and radiolabel. A particular bifunctional chelating agent is specified, cyclic anhydride of diethylene triaminepentaacetic acid. This teaching is thus limited, in that bifunctional chelate methods are characteristically complex, difficult to perform, require excessive time to accomplish radiolabeling, and yield less than optimal results.

The invention is further illustrated by the following non-limiting examples.

EXAMPLE I

Anti-SSEA-1 antibody was produced by either the MCA-480 or B37.2.1 cell lines in murine ascites by Charles River Biotechnology Services. The ascites was purified by ion exchange filter chromatography followed by column chromatography.

The purified IgM antibody was gently reduced using a solid phase disulfide reducing column. A column from a Pierce (Rockford, IL) protein reducing kit No. 77700 G was equilibrated with 10 ml of glycine buffer (10 mM glycine/NaOH buffer in 0.15 M NaCl, pH 8.3, nitrogen purged), and then activated with 10 ml of 10 mM dithiothreitol in glycine buffer. The column was then washed to remove the dithiothreitol with 20 ml of the glycine buffer. 1 ml of anti-SSEA-1 in a saline buffer at pH 8.3 at a concentration of 5 mg/ml was loaded on the column. The column was then stopped, 1 ml of glycine buffer added, and the column and contents allowed to incubate for one hour at room temperature. Following incubation, the reduced protein was eluted using 5 ml of glycine buffer in 1 ml aliquots, with the reduced protein fractions monitored by measuring absorbance at 280 nm. A nitrogen purged solution of 40 mM phthalate, 10 mM tartrate buffer. pH 5.5, with 1.25 mM stannous tartrate, was prepared, and radiolabeling kits made by adding 150 HI of the stannous tartrate radiolabeling solution to each 0.5 mg of reduced protein fraction. The kits were then yielded and immediately frozen or lyophilized.

To label the antibody, 2.5 mCi of $^{99m}$Tc in 0.25 ml of saline was added and the mixture allowed to incubate at room temperature for 30 minutes. The $^{99m}$Tc-labeled antibody was analyzed by quantitative, size exclusion, high performance liquid chromatography using a TSKG3000 column and TSK-pre column. The column effluent was analyzed for gamma radioactivity and optical density measured as 280 nanometers. The $^{99m}$Tc-labeled antibody was then incubated with 10 mM DTPA in phosphate buffered saline for 1 hour at 37° C. to determine if the $^{99m}$Tc label was vulnerable to removal by transchelation. The $^{99m}$Tc radioactivity eluted simultaneously with the IgMo The elution pattern was not altered by the incubation with DTPA indicating that the $^{99m}$Tc was firmly bound to the IgM protein. The $^{99m}$Tc-labeled antibody was incubated with solid phase antigen: the specific binding of the $^{99m}$Tc-labeled antibody to the solid phase was 59%.

EXAMPLE II

Purified IgM antibody is reduced by 10 mM dithiothreitol (DTT) in 10 mM glycine buffered saline at pH 8.0 for 60 minutes at room temperature and 37° C. A nitrogen purged solution of 40 mM phthalate, 10 mM sodium tartrate, pH 5.5, with 7.25 mM stannous tartrate is prepared. For each 1 ml of the DTT reduced antibody solution 2 ml of the stannous tartrate solution is added and a precipitate allowed to form and incubate for 1 hour at room temperature. The precipitate is compacted by centrifugation, under nitrogen gas, for 10 minutes and the supernatant removed and chromatographed using a size exclusion chromatography column packed with Sephadex using 10 mM glycine, 10 mM inositol, 20 mM sodium phthalate, and 5 mM sodium tartrate at pH 5.6. The molecular weight fraction corresponding to 125,000 to 200,000 Daltons is collected separately and concentrated by lyophilization. The protein concentration of an aliquot of lyophilized antibody fragments is determined. Nitrogen purged, 1.25 mM stannous tartrate in 20 mM sodium phthalate and 5 mM sodium tartrate at pH 5.6 is added so that the final product contained 22 μgm of stannous ion per 0.25 mg of protein. Aliquots of 0.25 mg of protein is placed in serum vials and either frozen or lyophilized.

To label the antibody, 2.5 mCi of $^{99m}$Tc in 0.25 ml of saline is added and the mixture allowed to incubate at room temperature for 30 minutes. The $^{99m}$Tc-labeled IgM antibody fragments is analyzed as in Example I. The $^{99m}$Tc radioactivity coelutes with the antibody fragment by HPLC and the specific binding of the $^{99m}$Tc-labeled fragment to solid phase antigen is 60±10%.

The preceding examples can be repeated with similar success by substituting the generically or specifically described reactants and/or operating conditions of this invention for those used in the preceding examples.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

What is claimed is:

1. A method of radiolabeling antibody against stage specific embryonic antigen-1 with a radionuclide to obtain stable labeling, comprising the steps of:
    a) incubating the antibody against stage specific embryonic antigen-1 with a Sn (II) agent, the period of incubation being sufficient to reduce available disulfide bonds to thiolate groups and allow formation of Sn (II)-containing and sulfur-containing complexes, while preventing excessive fragmentation of the antibody;
    b) purifying the reduced antibody to remove uncomplexed Sn (II) agents and other impurities yet retaining Sn (II) in a sufficient amount to reduce the radionuclide and not generate significant radiochemical impurities, the radionuclide to be added in a subsequent step; and
    c) radiolabeling the purified antibody with the Sn (II)-containing and sulfur-containing complexes by adding the radionuclide, whereby the Sn (II) agent reduces the radionuclide and the reduced radionuclide forms radionuclide-containing and sulfur-containing complexes.

2. The method of claim 1 wherein the source of Sn (II) agent is present in a solution comprising alkali metal tartrate having a pH of between approximately 5.0 and 6.0.

3. The method of claim 1 wherein the source of Sn (II) agent comprises a member selected from the group consisting of stannous tartrate, stannous glucoheptonate, stannous gluconate, stannous phosphonate, stannous chloride, and stannous fluoride.

4. The method of claim 1 wherein the antibody against stage specific embryonic antigen-1 is a product of the MCA-480 hybridoma.

5. The method of claim 1 wherein following step b), prior to step c), the purified antibody with Sn (II)-containing and sulfur-containing complexes is frozen in a vial, whereby the frozen purified antibody with Sn (II)-containing and sulfur-containing complexes can be maintained for an indefinite period before radiolabeling in step c) by the addition of the radionuclide to the vial.

6. The method of claim 1 wherein following step b), and prior to step c), the purified antibody with Sn (II)-containing and sulfur-containing complexes is lyophilized in a vial, whereby the lyophilized purified antibody with Sn (II)-containing and sulfur-containing complexes can be maintained for an indefinite period before radiolabeling in step c) by the addition of the radionuclide to the vial.

7. The method of claim 1 wherein 85 percent or more of the radionuclide is strongly bonded to the antibody.

8. The method of claim 1 wherein the radionuclide is technetium-99m in the form of sodium pertechnetate.

9. The method of claim 1 wherein the radionuclide comprises a member selected from the group consisting of radioisotopes of indium, gold, silver, mercury, technetium, rhenium and copper.

10. A method of producing reduced oxidation resistant intact antibody against stage specific embryonic antigen-1 for subsequent labeling with a radionuclide to obtain stable labeling, comprising the ordered steps of:
    a) incubating the intact antibody against stage specific embryonic antigen-1 with a first reducing agent, the period of incubation being sufficient to reduce available disulfide bonds to thiolate groups while preventing excessive fragmentation of the antibody;
    b) adding a source of first Sn (II) agent to the reduced intact antibody in a sufficient amount to form Sn (II)-containing and sulfurcontaining complexes, resulting in formation of complexes between sulfur and Sn (II) which protect against subsequent reoxidation prior to purification and radiolabeling, the reduced intact antibody to purified in a subsequent step, and the radionuclide to be added in a subsequent step;
    c) purifying the rescued intact antibody to substantially remove the first reducing agent and impurities;
    d) freezing the purified reduced intact antibody containing Sn (II)-containing and sulfur-containing complexes in a vial, whereby the frozen purified reduced antibody containing Sn(II)-containing and sulfur-containing complexes can be maintained for an indefinite period before radiolabeling by the addition of the radionuclide; and
    e) radiolabeling the purified reduced intact antibody by adding the radionuclide, whereby the complexed first Sn(II) agent reduces the radionuclide and the reduced radionuclide and reduced antibody form stable radionuclide-containing and sulfur-containing complexes.

11. The method of claim 10 wherein the first reducing agent comprises at least one member selected from the group consisting of 2-mercaptoethanol; 1,4 dithiothreitol; 2,3 dihydroxybutane-1; 4 dithiol; 2-aminoethanethiol HCl; 2-mercaptoethylamine; thioglycolate; cyanide; cysteine; reduced gluthaione; Sn(II); Cu(I); and Ti(II).

12. The method of claim 10 wherein the first reducing agent is attached to a solid phase.

13. The method of claim 10 wherein the source of first Sn(II) agent is present in a solution comprising alkali metal tartrate having a pH of between approximately 5.0 to 6.0.

14. The method of claim 10 wherein the source of first Sn(II) agent comprises a member selected from the group consisting of stannous tartrate, stannous glucoheptonate, stannous gluconate, stannous phosphonate, stannous chloride, and stannous fluoride.

15. The method of claim 10 wherein the antibody against stage specific embryonic antigen-1 is a product of the MCA-480 hybridoma.

16. The method of claim 10 wherein following step c), and prior to step d), a second Sn(II) agent is added to the purified reduced intact antibody containing Sn(II)-containing and sulfur-containing complexes in a sufficient amount to completely reduce the radionuclide, whereby the reduced radionuclide and reduced antibody form stable radionuclide-containing and sulfur-containing complexes.

17. The method of claim 10 wherein following step d), and prior to step e), the frozen purified reduced intact antibody with Sn(II) agent is lyophilized in a vial, whereby the lyophilized purified reduced antibody with Sn(II) agent can be maintained for an indefinite period before radiolabeling in step e) by the addition of the radionuclide to the vial.

18. The method of claim 18 wherein 85 percent or more of the radionuclide is strongly bonded to the antibody.

19. The method of claim 10 wherein the radionuclide is technetium-99m in the form of sodium pertechnetate.

20. The method of claim 10 wherein the radionuclide comprises a member selected from the group consisting of radioisotopes of indium, gold, silver, mercury, technetium, rhenium and copper.

* * * * *